United States Patent [19]

Brun et al.

[11] Patent Number: 4,562,715

[45] Date of Patent: Jan. 7, 1986

[54] PROCESS AND APPARATUS FOR DETERMINING THE QUALITY OF A THIN COATED OR UNCOATED STEEL SHEET

[75] Inventors: Charles G. H. Brun, Montataire; Jean F. Bailleul; Freddy Lecendre, both of Grande-Synthe; Francoise Coolen, Dunkerque, all of France

[73] Assignee: Union Siderurgique du Nord et de l'Est de la France, Puteaux, France

[21] Appl. No.: 608,592

[22] Filed: May 9, 1984

[30] Foreign Application Priority Data

May 9, 1983 [FR] France .................................. 83 07719

[51] Int. Cl.⁴ ........................ B21D 11/08; B21D 22/00
[52] U.S. Cl. ........................................ 72/167; 72/347; 72/379
[58] Field of Search .................. 72/166, 167, 183, 379, 72/347, 350, 377

[56] References Cited

U.S. PATENT DOCUMENTS 4,432,222 2/1984 Ujihara ................................ 72/379

Primary Examiner—W. D. Bray
Attorney, Agent, or Firm—Cushman, Darby & Cushman

[57] ABSTRACT

The process is in particular intended for the manufacture of tinplate and comprises cutting a strip in the direction transverse to the direction of rolling of a reel of steel sheet, subjecting said strip to a drawing action by compression while bending the strip, and examining possible cracking on the surface of the drawn strip. This process is carried out in an apparatus which comprises a frame 1 supporting means 2 for pulling a steel strip and a head 4 for effecting a drawing action by compression while bending the strip. The head is connected to the frame and the steel strip 3 is passed through the head under the action of the pulling means 2.

9 Claims, 2 Drawing Figures

PROCESS AND APPARATUS FOR DETERMINING THE QUALITY OF A THIN COATED OR UNCOATED STEEL SHEET

The present invention relates to a process and apparatus for determining the quality of a coated or uncoated thin steel sheet and in particular a steel sheet for producing tinplate of the type for stamping and drawing.

Tinplate or tinned iron of the quality for stamping and drawing is intended for the manufacture of cans or boxes for preserving food or beverages by means of a process in which the body of the can is produced by a stamping operation producing a cup and a drawing of the walls and then a curling over of the upper edge portions.

These operations subject the metal to shear forces in the lateral walls of the can while the curling over operation on the edge portions effected on the deformed metal is also critical if an unsplit, even edge portion is to be obtained. The internal defects in the metal may result, under these severe stamping and drawing operations, in the formation of cracking in the walls of the can or the curled-over edge portion so that the metal is unsuitable for manufacturing such cans.

There are already known from the Pat. No. FR-A-740 502 a process and apparatus for determining the aptitude of metal sheets to be stamped, by means of a tensile test which subjects simultaneously the specimen to a folding and a straightening under the action of one or more fingers which move alternately along the test specimen which is maintained under tensile stress at each of its ends until the specimen fractures.

However, such a process does not permit the determination of the inclusional state of the steel, i.e. the quality of this steel as concerns its content of inclusions, which is quite essential in the envisaged application.

There is therefore needed a process for determining the quality of the initial iron sheet which must be subjected to a tinning process for producing tinplate before manufacturing the cans or boxes.

An object of the present invention is to provide such a process for determining the quality of a steel sheet, in particular for producing tinplate of the type for stamping and drawing operations, and an apparatus for carrying out this process.

The invention therefore provides a process for determining the quality of a coated or uncoated thin steel sheet comprising cutting a strip in the transverse direction relative to the rolling direction of a reel of steel sheet, subjecting said strip to drawing conditions by compression while bending at the point of compression, and examining the possible cracking which may appear on the surface of the drawn strip. The drawing of the strip is achieved by compressing the strip throughout its width between two jaws, the distance between which is less than the thickness of the strip and causing said strip to undergo a change in direction at the point of compression so as to achieve the drawing and bending.

The drawing is achieved in one or several passes so as to obtain a total elongation of 5 to 30% of the strip.

The steel strip is cut to a width of 2 to 10 cms and a length equal to the width of the reel.

The process of the present invention applies in particular to the examination of the quality of a steel sheet intended for manufacturing tinplate for example of the quality for stamping and drawing operations.

Another object of the invention is to provide a device for carrying out the process defined hereinbefore, said device comprising a frame supporting means for exerting tensile stress on a steel strip and a head for exerting a drawing and bending operation connected to the frame and through which head the steel strip is made to pass under the action of pulling means.

The head for effecting a drawing and bending operation comprises two jaws which exert a compression action on the strip while it is at the same time subjected to a change in direction.

According to a feature of this device, the drawing and bending head comprises two movable opposed male and female jaws, the male jaw having a planar surface from which projects a semi-cylindrical form whose axis is perpendicular to the direction of displacement of the strip, the female jaw having a planar surface in which is formed a substantially semi-cylindrical groove whose axis is parallel to the axis of the projecting portion of the male jaw and disposed in the same vertical plane, but slightly set back relative to the surface of the female jaw so as to exert a compressing and bending action on the strip.

The invention will be described in detail hereinafter with reference to the accompanying drawings which show only one embodiment.

In these drawings

Figure 1:
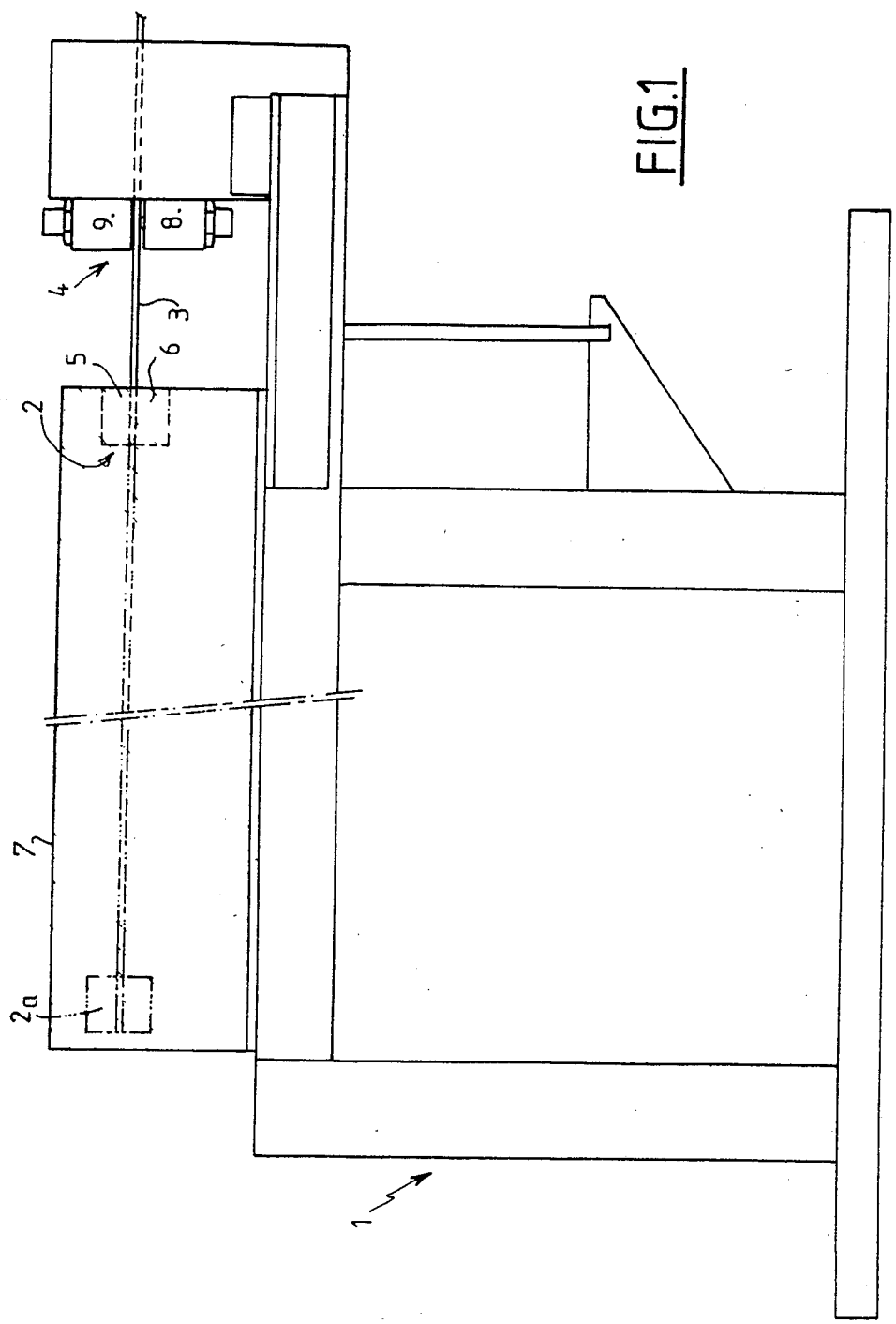
FIG. 1 is an elevational view of the machine for determining the quality of the steel, of the type for stamping and drawing.
Figure 2:
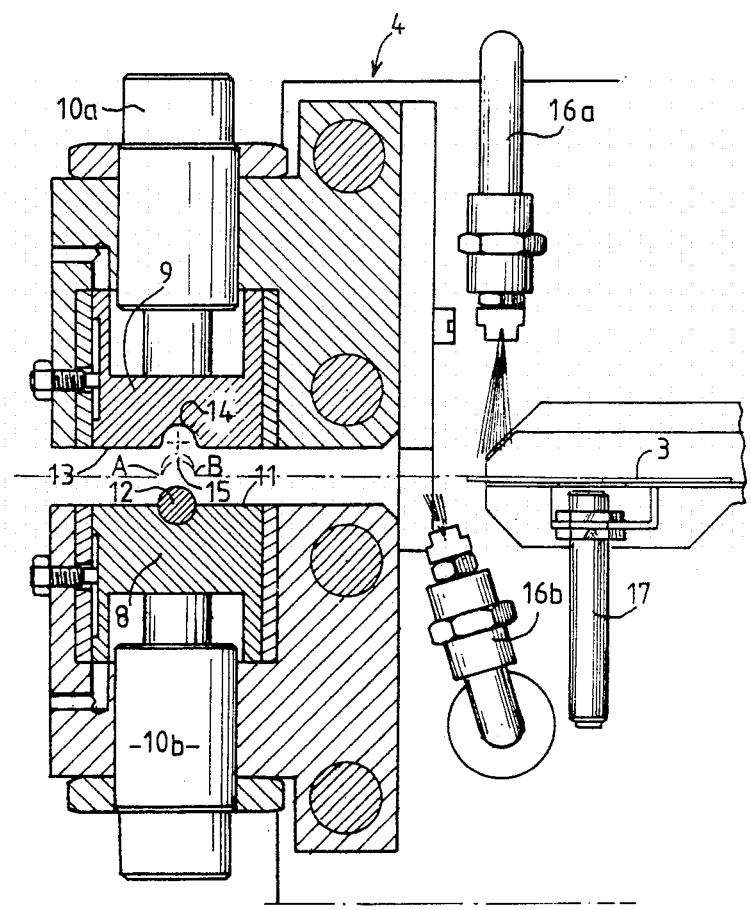
FIG. 2 is a sectional view of the drawing and bending head of the machine shown in FIG. 1.

The test machine shown in FIG. 1 comprises a frame 1 supporting means 2 for pulling a strip 3 which is subjected to a drawing and bending action in a head 4.

The supporting and pulling means 2, which are neither described nor illustrated in detail since they are well known in the art, comprise gripping jaws 5 and 6 which grip the strip 3 at one end and move in horizontal translation in a protecting tunnel 7 to a position shown at 2a. The strip 3 passes into the head 4 while being inserted therein from the right of the Figure and then gripped between the gripping jaws 5 and 6.

The drawing and bending head 4 comprises a male jaw 8 and a female jaw 9 which are in opposed relation and are capable of being moved toward and away from each other by means of jacks 10a, 10b mounted in the head 4 which is connected to the frame 1.

The male jaw 8 has a planar surface 11 from which projects a punch 12 of semi-cylindrical shape, whose axis is located in the plane of the surface 11 and perpendicular to the direction of displacement of the strip.

The female jaw 9 has a planar surface 13 parallel to the surface 11 and facing the latter and includes a substantially semi-cylindrical groove 14 whose axis is parallel to the axis of the punch 12 and located in the same vertical plane, but slightly set back from the surface 13 so as to exert throughout the width of the strip 3 in the course of the test a compression effect while bending the strip along two generatrices of the punch 12 corresponding to the points A and B.

When the jaws 8 and 9 are moved toward each other until the surfaces 11 and 13 are in contact with each other, a space 15 remains between the punch 12 and the bottom of the groove 14, this space being greater than the thickness of the strip 3 to be tested.

At points A and B, the strip is subjected to a stress by compression while it is bent throughout its width, which constitutes the essential feature of the invention.

The machine further comprises spraying lubricating means 16a and 16b supplying a lubricant to the upper and lower surfaces respectively of the strip 3.

The jacks are supplied, in a conventional manner, with a hydraulic fluid (not shown) and the machine includes end-of-travel stop means 17 for the drawing of the strip.

In operation of the machine, the strip 13 is first inserted between the jaws 8 and 9 (which are moved apart) of the bending and drawing head 4 and then gripped between the gripping jaws 5 and 6 of the pulling means. The drawing and bending head jaws are then caused to grip the strip and a pull is exerted on the strip 3 by the means 2 so as to pass it through the head 4 under the stress conditions defined hereinbefore.

The strip is previously lubricated before it passes into the head 4.

The strip 3 is passed through the machine one or several times so as to obtain an elongation of 5 to 30%.

The drawn sheet is then examined by eye so as to determine the presence of possible elongated cracking having a length of the order of 0.5 to 5 mm in the direction corresponding to the rolling direction of the strip and which would reveal the presence of inclusions.

The process for determining the quality of the blank sheet and the apparatus for carrying out said process, which is of simple design, permit rapidly revealing defects in the form of inclusions embedded within the mass of the sheet and therefore an elimination of the reel in respect of which the quality of the steel is unsatisfactory for the envisaged use. In this way, there is in particular avoided the manufacture of tinplate sheets whose defective quality would only be noticeable at the moment of manufacturing the finished product, i.e. by the obtainment of stamped and drawn boxes or cans whose walls include splits or cracking and whose formed-over edge portions are split. The process according to the invention therefore results in very considerable economy.

It will be understood that the test may also be carried on the coated metal sheet so as to check the quality of the tinplate as concerns its inclusional property which determines its aptitude to produce the aforementioned boxes or cans.

What is claimed is:

1. A process for determining the quality of a thin steel sheet, said process comprising cutting a strip in a direction transverse to a direction of rolling of a reel of steel sheet, subjecting said strip to a drawing operation by passing said strip longitudinally in a given direction between a first structure having two edges defining a space which is substantially perpendicular to said given direction, and a second structure defining a projection substantially perpendicular to said given direction, while urging said two structures toward each other so as to cause said projection to enter said space with said strip interposed between said projection and said two edges and thereby compress said strip between said two edges and said projection and cause said strip to bend along said edges, and simultaneously pulling on said strip so as to draw it between said projection and said two edges, and subsequently searching for cracking which might appear on the surface of the draw strip.

2. A process according to claim 1, comprising subjecting the strip to a total elongation of 5 to 30% in at least one pass through said two structures.

3. A process according to claim 1, wherein the cut steel strip has a width of 2 to 10 cms and a length equal to the width of the reel.

4. A process according to claim 1, wherein said sheet is a coated sheet.

5. A process according to claim 1, wherein said sheet is an uncoated sheet.

6. An apparatus for determining the quality of a thin steel sheet, said apparatus comprising a frame, pulling means for pulling on the steel strip in a given direction and carried by said frame, and a head for effecting a drawing of the sheet by compression and a bending of the sheet and connected to said frame and through which head the steel strip is passed under the action of said pulling means, said head comprising a first structure having two edges defining a space which extends substantially perpendicularly to said given direction, and a second structure having a projection which extends substantially perpendicularly to said given direction, said two structures being movable toward and away from each other and said projection being capable of entering said space and coming into contact with said two edges, and means for urging said two structures toward each other under pressure for the purpose of compressing said sheet between said projection and said two edges of said first structure.

7. An apparatus according to claim 6, wherein the second structure comprises a male jaw having a planar surface and a semi-cylindrical portion which projects from said planar surface and has an axis which is perpendicular to said given direction of pulling of the strip, said first structure comprising a female jaw having a planar surface and a substantially semi-cylindrical groove which defines said two edges and is provided in the planar surface of the female jaw and has an axis which is parallel to said axis of the projecting portion of the male jaw and is contained in the same vertical plane as said axis of said projecting portion, said axis of said groove being slightly set back relative to the surface of the female jaw so that when the two jaws are moved toward each other said edges of said groove are capable of engaging said projection on opposite sides of sdid projection while the groove is spaced away from said projection in the rest of said groove.

8. An apparatus according to claim 6, comprising upstream of the head relative to said given direction lubricating means for lubricating opposed sides of the strip.

9. An apparatus according to claim 7, wherein said projecting portion and said groove define a crescent-shaped space therebetween when said two edges engage said opposite sides of said projection.

* * * * *